United States Patent [19]
Kiczka

[11] Patent Number: 6,123,937
[45] Date of Patent: Sep. 26, 2000

[54] APPLICATIONS OF LYSOZYME DIMER

[75] Inventor: Witold Kiczka, Princeton, N.J.

[73] Assignee: Nika Health Products, Limited, Vaduz, Liechtenstein

[21] Appl. No.: 08/885,849

[22] Filed: Jun. 30, 1997

Related U.S. Application Data

[63] Continuation-in-part of application No. 08/815,009, Mar. 14, 1997, abandoned.

[51] Int. Cl.[7] .................................................. A61K 38/47
[52] U.S. Cl. ............................................ 424/94.61
[58] Field of Search ............................... 424/94.1, 94.61

[56] References Cited

U.S. PATENT DOCUMENTS

| | | |
|---|---|---|
| 5,118,500 | 6/1992 | Hanel et al. . |
| 5,260,182 | 11/1993 | Nagaoka et al. . |
| 5,314,816 | 5/1994 | Uermann et al. . |
| 5,317,019 | 5/1994 | Bender et al. . |
| 5,420,154 | 5/1995 | Christensen, IV et al. . |
| 5,466,449 | 11/1995 | Kiczka . |

FOREIGN PATENT DOCUMENTS

| | | |
|---|---|---|
| 0-181634 | 5/1986 | European Pat. Off. . |
| 4.020 | 4/1966 | France . |
| 2215201 | 8/1974 | France . |
| 55-033408 | 3/1980 | Japan . |
| 55-033409 | 3/1980 | Japan . |
| 55-043040 | 3/1980 | Japan . |
| WO 89/11294 | 11/1989 | WIPO . |
| WO 91/10731 | 7/1991 | WIPO . |
| WO 94/01127 | 1/1994 | WIPO . |
| WO 96/21463 | 7/1996 | WIPO . |

OTHER PUBLICATIONS

Bartholyns et all. "In Vitro and In Vivo Antitumor Effect of Dimerized Ribonuclease A*."*European Journal of Cancer*, v15, pp. 85–91, 1979.

Sorrentino et al. "Dimerization of Deoxyribonuclease I, Lysozyme and Papain." *European Journal of Biochemistry*, v124, pp. 183–189, 1982.

Malinowski, E. et al. "A New Method of Treatment of Cystic Ovary Disease with Lydium–KLP." 13th International Congress on Animal Reproduction, Sydney, Australia, Jun. 30–Jul. 4, 1996.

Katsutoshi Takada et al., "Binding of Lysozyme to Lipopolysaccharide Suppresses Tumor Necrosis Factor Production In Vivo," *Infection and Immunity*, vol. 62, No. 4, pp. 1171–1175, 1994.

Ana J. Coito et al., "Anti–TNF–α Treatment Down–Regulates the Expression of Fibronectin and Decreases Cellular Infiltration of Cardiac. Allografts in Rats[1]," *Journal of Immunology*, vol. 154, pp. 2949–2958, 1995.

J. Bartholeyns, et al., Archives Internationales de Physiologie et de Biochimie, vol. 87(1), p. 155–156 (Feb. 1979).

Annapurna Vyakarnam et al., "Tumour Necrosis Factors (α, β) Induced by HIV–1 in Peripheral Blood Mononuclear Cells Potentiate Virus Replication," *AIDS*, vol. 4, No. 1, pp. 21–27, 1990.

Katherine F. Bayston et al., "Bacterial Endotoxin and Current Concepts in the Diagnosis and Treatment of Endotoxaemia," *J. Med. Microbiol.*, vol. 31, pp. 73–83, 1990.

Dennis L. Stevens et al., "Gram–positive Shock," *Current Opinion in Infectious Diseases*, vol. 5, pp. 355–363, 1992.

Frank E. Berkowitz, "Bacterial Toxins in the Pathogenesis of Infections," *Current Opinion in Infectious Diseases*, vol. 4, pp. 332–337, 1991.

Philip A. Mackowiak, "Mechanism of Fever," *Current Opinion in Infectious Diseases*, vol. 5, pp. 348–354, 1992.

Toshifumi Matsuyama et al., "Cytokines and HIV Infection: Is AIDS a Tumor Necrosis Factor Disease?," *AIDS*, vol. 5, pp. 1405–1417, 1991.

Masahiko Ito et al., "Tumor Necrosis Factor Antagonizes Inhibitory Effect of Azidothymidine on Human Immunodeficiency Virus (HIV) Replication In Vitro," *Biochemical and Biophysical Research Communications*, vol. 166, No. 3, pp. 1095–1101, Feb. 14, 1990.

Dembinski et al., Zycie Weterynaryjne 4A, pp. 164–168, 1994.

Dembinski et al., Acta Academie Agriculturae ac Technicae Olstenensis, Veterinaria, No. 23: 201–207, 1996.

Dembinski et al., "Application of lydium KLP dimer of lysozyme in the prophalaxis and treatment of coliform mastitis in sows", Proceedings of the 13th International Pig Veterinary Society Congress, Bangkok, Thailand, Jun. 1994.

Malinowski et al., Medycyna Weterynaryjna, vol. 51 (6): 351–353, 1995.

Dembinski, et al., "Application of Lydium KLP (Dimer of Lysozyme) in Treatment of Inflammation of Endometrium in Cows", Proceedings 18th World Buiatrics Congress: 26th Congress of the Italian Association of Buiatrics, Bologna Italy, vol. 1, pp. 321–324, 1994.

*Primary Examiner*—Yvonne Eyler
*Assistant Examiner*—Brenda Brumback
*Attorney, Agent, or Firm*—Oliff & Berridge, PLC

[57] ABSTRACT

A method for prophylactic or therapeutic treatment of a disease or bodily condition that is caused or affected by a hormonal or metabolic disorder, such as cystic ovarian disease, temporary infertility, permanent infertility, lack of menstrual cycles, irregular menstrual cycles, and nymphomania, includes administering to a mammal a lysozyme dimer in an amount effective for preventing or treating said disease or condition.

11 Claims, 2 Drawing Sheets

APPLICATIONS OF LYSOZYME DIMER

This application is a Continuation-In-Part of U.S. application Ser. No. 08/815,009, now abandoned filed Mar. 14, 1997.

BACKGROUND OF THE INVENTION

The present invention relates to a new application of lysozyme dimer. In particular, the present invention relates to a method for the prevention or therapeutic treatment of a disease or bodily condition of a mammal, which disease or condition is directly caused or affected by a hormonal or metabolic disorder such as, in particular, cystic ovarian disease.

In the late 1980s, it was discovered that the isolated dimerized forms of certain enzymes, while substantially retaining the beneficial properties of the corresponding monomers, turned to be by far less toxic than the monomers themselves and in some instances did not even display negative side effects at all when used in therapeutic doses. Antiviral and antibacterial compositions comprising as the active ingredient lysozyme dimer or other dimerized enzymes have been described in WO 89/11294, the entire disclosure of which is incorporated herein by reference. It is reported therein that lysozyme dimer is capable of inhibiting proliferation of a number of bacterial strains cultivated on samples taken from patients, when applied in concentrations of 1.25–20 mg/ml of the culture. It is also reported that the dimer is effective in treating canine parvovirus (CPV) infections when administered orally twice a day at a dose of 1–2 mg/kg of body weight. Later on, further attractive features of lysozyme dimers were found and additional therapeutical applications of the drug were developed, especially for the treatment of bacterial and viral infections as disclosed, for instance, in WO 94/01127, the entire disclosure of which is incorporated herein by reference.

In WO 94/01127, a model theory is presented that can help to understand the different effects observed with the lysozyme dimer. Although the entire mode of action of the lysozyme dimer is not yet fully understood, it appears that there is additional curative capability that cannot be explained by the bacteriolytic activity of the corresponding monomer. The inventors observed certain immunostimulative effects of the dimerized lysozyme, particularly concerning the modulation of cytokine levels. Moreover, from their experiments, they concluded that lysozyme dimer seems to prevent the penetration of bacterial cells by viruses, presumably by blocking certain regions of the outer cell surface and probably comprising virus receptor proteins.

The inventor observed certain immunostimulative effects of the dimerized lysozyme, particularly concerning the modulation of cytokine levels, confirmed by in vitro and in vivo experiments. The lysozyme dimer is able, amongst others, to modulate the synthesis of TNFΔ, IL-2, IL-6 and INFα, and to activate phagocytosis and the immunological mechanisms connected therewith. The lysozyme dimer is in particular useful for the treatment and prophylaxis of diseases associated with excessively high levels of TNFα.

The prior art discloses further results obtained in vitro with lysozyme dimer. Particularly, Bartholeyns and Zenebergh (Europ. J. Cancer, Vol. 15, 1979, 85–91) tested dimerized lysozyme for cytostatic activities against liver cancer cells (HCT) in vitro. They observed a 73% ±15% inhibition of cancer cell multiplication in the cell culture (ibid., p.89, Table 2).

Surprisingly, except for WO 94/01127, no in vivo experiments with lysozyme dimer are reported so far. It is very strange and astonishing, and up to now waits for explanation, why neither Bartholeyns and Zenebergh nor any other researcher resumed this subject to promote further development of a promising discovery to combat cancer. A comparative showing (FIG. 3) of the purity of lysozyme dimer produced according to the method of Sorrentino et al., Eur. J. Biochem. 124, 183–189 (1982) and of the lysozyme dimer preferably used in the present invention revealed at least one possible reason: high concentrations of by-products such as lysozyme monomer, trimer and tetramer are found in the preparation produced according to Sorrentino et al., whereas the product preferably used in the present invention is highly purified, i.e., contains the desired lysozyme dimer in amounts of up to 90% or more by weight of the total lysozyme fraction of the preparation. A process for the manufacture of such highly purified lysozyme dimer has been described in WO 91/10731, the entire disclosure of which is incorporated herein by reference. This strongly supports the assumption that the purity of the prior art lysozyme dimer was simply not good enough for in vivo experiments and applications because it was known in the art already over 15 years ago that the monomeric form of lysozyme, despite its beneficial antibacterial activity, is rather toxic and can cause inflammations and severe allergies and even toxic shock symptoms.

In light of such circumstances it appears more understandable why no competent researcher including Bartholeyns and Zenebergh—although recommending lysozyme dimer as a promising candidate for further investigations—has carried out further experiments during the past ten to fifteen years to develop lysozyme dimer applications in vivo.

In spite of such lack of research activities of the scientific world possibly due to a prejudice of the art against the use of lysozyme dimer in vivo, the present inventors carried out further research and developmental work to improve the method of production and purification of the dimerized lysozyme and to find in vivo human and animal applications for the product, which led, for instance, to the antiviral and antibacterial and TNF level modulating applications disclosed in WO 94/01127, and the entire disclosure of which is incorporated herein by reference.

It could also be successfully demonstrated that lysozyme dimer compositions display remarkable potency in the inhibition or even total prevention of leukemic cell proliferation in vivo, particularly in the case of virus induced lymphatic leukemia. Further investigations led to the manufacture of pharmaceutical compositions comprising lysozyme dimer as the active component applicable in cases of hair growth disorders, particularly hair growth disorders based on immunological malfunctions or dysfunctions, or in preventing or treating diseases connected with a suppressed immune system. Such compositions, and their applications, are described in U.S. Patent applications Ser. Nos. 08/815,009 and 08/351,375 and International application Ser. No. PCT/EP96/00135, the entire disclosures of which are incorporated herein by reference.

Use of immunostimulants, adjuvants and vaccines offers a wide range of attractive methods for inducing and building up protection against diseases. In this respect, "immunostimulants" refer to compounds that only stimulate non-specific defense mechanisms and protect against diseases. "Immunomodulators" refer to compounds that regulate (or modulate) the defense mechanisms after suppression (or decrease of immunity) of those mechanisms. Such suppression can arise from or be induced by many sources including pollutants, chemotherapeutics, stress, food, temperature changes, and the like. Immunomodulators stabilize the defense mechanisms after the influence of pathogens, and increase cellular and humoral immunity. Some immunomodulators are also able to depress and/or normalize hyperactive defense mechanisms including modulation of cytokine levels. Many immunostimulants are also classified as immunomodulators.

Moreover, based on their knowledge of low toxicity of dimerized lysozyme compared to the monomer. and on the availability of a new, highly purified lysozyme dimer preparation, the present inventors attempted and started anti-cancer trials with lysozyme dimer preparations in vivo, although the prior art did not suggest its use to treat diseases other than bacterial or viral infections.

Further investigative work by the present inventors has also revealed additional advantageous uses of the lysozyme dimer. Recent studies on immunomodulating properties of the lysozyme dimers have shown that it potentiates humoral response in mammals. In particular, the lysozyme dimer has been found to have the unexpected advantage of being capable of positively affecting the primary humoral response of mammals immunized with an antigen after immunosuppression. Such immunomodulating properties of the lysozyme dimer were not taught or suggested by the prior art.

SUMMARY OF THE INVENTION

Cystic ovarian disease (COD) has been identified as one of the main causes of bovine infertility or fertility disorders. The COD was noted in 10 to 50% of the animals during the postcalving period. Among others, an insufficient immune system and metabolic disorders have been recognized as major risk factors for the development of COD. The treatment of COD by administering hormones like GnRH, progesterone or prostaglandine is not always effective.

It is an object of the present invention to provide a method for the prophylactic or therapeutic treatment of COD by administering to a mammal at risk of or subject to COD an effective dose of a highly purified lysozyme dimer, preferably containing 10% wt. or less of unintended by-products and being substantially free of monomeric lysozyme. It could successfully be demonstrated in vivo that the efficacy of the COD treatment with Lydium-KLP comprising lysozyme dimer as the active ingredient was clearly better than with conventional hormone injections.

The term Lydium-KLP used herein refers to a commercially available product of Nika Health Products, Ltd., Poland, and refers to a liquid composition, preferably an injection solution, comprising the aforementioned highly purified lysozyme dimer at a concentration of 0.01 to 10 mg per 1 ml of the solution.

These and other advantages are provided by the present invention.

DETAILED DESCRIPTION OF PREFERRED EMBODIMENTS

Figure 1:
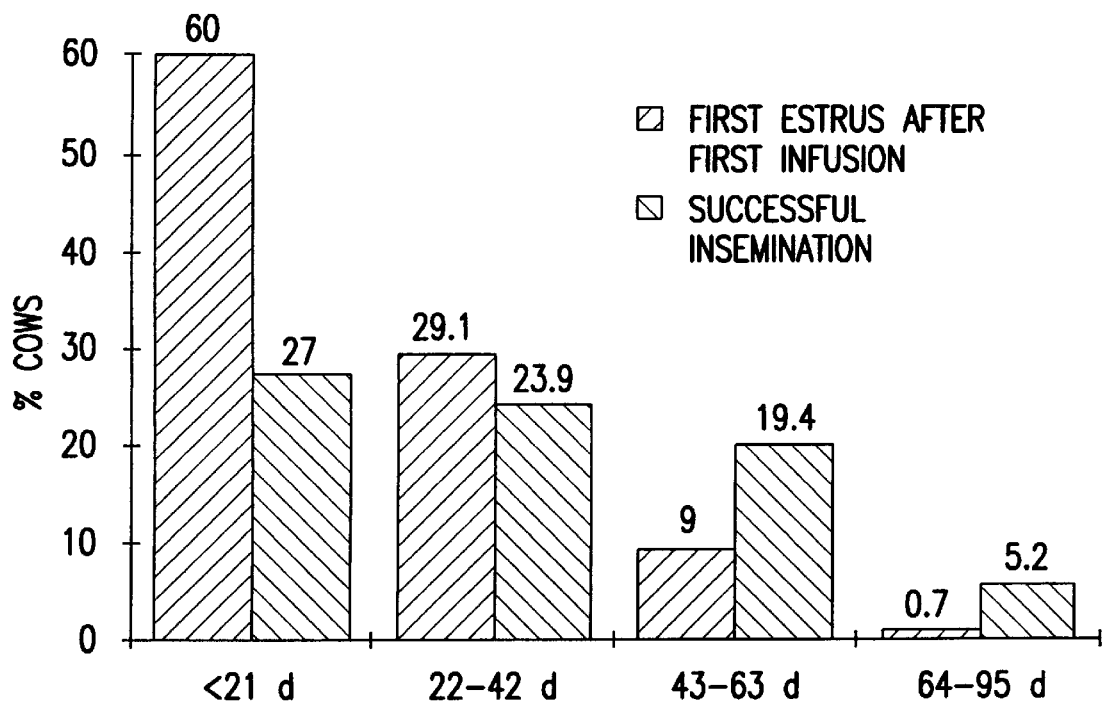
FIG. 1 shows the time of the first heat and the percentage of conceived cows as a result of successful insemination in the first or second heat following the first administration of Lydium-KLP.

The highly purified lysozyme dimer referred to in the present invention can be used for the manufacture of pharmaceutical compositions directly applicable for the treatment of animals, particularly mammals and humans, due to its low amount of toxic monomer.

As indicated above, such purified lysozyme dimer contains about 10% wt. or less of unintended by-products, and can be obtained via dimerization of lysozyme monomers of any origin, e.g. of lysozyme monomers derived from humans, animals, eggs, plants, microorganisms, the monomers being either naturally isolated in native form or manufactured via chemical or genetic engineering methods to yield lysozyme monomers of the same or essentially the same chemical and biological nature as the naturally occurring ones.

It is an object of the present invention to provide for a pharmaceutical composition and a method to prevent and/or treat COD, and similar or related diseases, disorders and conditions.

Therefore, it is an object of the present invention to provide for novel applications of lysozyme dimer comprising its use for the manufacture of a pharmaceutical composition for the prophylactic or therapeutic treatment of a disease or bodily condition that is caused or affected by a hormonal or metabolic disorder. In particular, the disease or bodily condition can include cystic ovarian disease, temporary infertility, permanent infertility, lack of menstrual cycle, irregular menstrual cycle, and nymphomania.

According to the methods of the present invention, it is preferable to treat the animal or mammal with the highly purified lysozyme dimer reported in WO 91/10731, which contains about 10% by weight or less of unintended by-products and which is essentially free from the monomeric form of lysozyme. However, it might also be acceptable to administer a lysozyme dimer preparation of lower purity as long as it is applied at a dose that does not cause adverse effects due to the presence of toxic by-products, especially Of lysozyme monomer.

The lysozyme dimer referred to in the present invention can advantageously, and quite unexpectedly, be used in methods for modulating hormone levels of animals. For example, the hormone level modulation can comprise the normalization of abnormally high or low progesterone levels. The lysozyme dimer can be applied directly, or preferably can be applied in the form of a pharmaceutical composition as will be described below. The lysozyme dimer can also be applied in the form of an intrauterine infusion.

In the present invention, the lysozyme dimer can be administered in one dose, or in several doses over a set treatment period. Preferably, the lysozyme dimer is administered in a series of multiple doses, for example two or three, over an established treatment period of, for example, between 12 to 48 hours and one to three, preferably two, weeks between doses. However, it will be understood by those skilled in the art, and based on the present disclosure, that the dosages and treatment periods will vary depending on particulars of the specific patient and treatment objectives.

For use in the treatment methods of the present invention, each dose of lysozyme dimer preferably contains from about 1.0 to about 100, preferably about 1 to about 50, and more preferably from about 2 to about 20, µg/kg total body weight.

The lysozyme dimer referred to herein can either directly be applied to the patients in need thereof or can be used for the manufacture of pharmaceutical compositions to be applied in usual galenic forms. Gels, ointments, or liquid compositions comprise the lysozyme dimer preferably in a concentration of about 0.01–10 mg/ml and frequently in a concentration of about 0.1–1.0 mg/ml. They are usually prepared as sterile and apyrogenic compositions and optionally further comprise at least one physiologically acceptable solvent and/or carrier and/or at least one suitable preservative.

The pharmaceutical compositions containing lysozyme dimer are useful and intended primarily for topical and/or parenteral application comprising local injection, or external applications on the surface of the body including subcutaneous injection. Intravenous injections may replace or additionally support topical applications in the course of a therapy. It has, however, also proven very efficient to administer lysozyme dimer compositions to mucosal membranes, preferably via inhalation (nasal, mouth, pharyngeal mucosa) of liquid compositions or topical application (e.g. vaginal, cervical mucosa) of liquid or creamy compositions or tampons impregnated with lysozyme dimer material.

In some cases it is preferred to apply the lysozyme dimer orally, preferably in usual galenic forms such as for instance tablets, capsules or dragees or in the form of pellets, granules, flocs or as a powder. These solid compositions frequently contain the active drug in an amount of about 0.01–10 mg, preferably about 0.01–1.0 mg per g of the total composition. It is also preferred that they further comprise at least one suitable carrier and/or preservative and/or other usual additives such as for instance a flavor or a colorant.

Similarly, intrauterine infusion of the lysozyme dimer can also be very useful and beneficial in the treatment methods of the present invention. Treatment according to the present invention can also include combined oral delivery and intrauterine infusion, if desired.

The various types of the above mentioned lysozyme dimer compositions are preferably administered in a single or repeatable dose of about 0.001 to 0.5 mg/kg of body weight, especially at a dose of about 0.01 to 0.1 mg/kg of body weight. It goes without saying that the required concentration of active lysozyme dimer in the final pharmaceutical composition depends primarily on the size of the human or animal patient and of the kind of therapy or prophylactic treatment scheduled for the concerned patient. In most cases, however, the above mentioned concentration ranges are sufficient for a proper treatment. Nevertheless, it might become necessary, particularly in veterinary medicine, to increase the actual lysozyme dimer concentrations in the composition to a value beyond the 10 mg/ml and below the solubility product of the dimer in the respective solvent, i.e. to about 20 mg/ml of liquid or ointment.

In doing so, the volume of the composition to be administered can be kept to a reasonable minimum for the ease of handling.

If possible, a combined administration protocol of the aforementioned compositions is preferred over a single therapy of either oral, parenteral or topical application.

Due to the essentially untoxic character of the highly purified lysozyme dimer, the compositions containing such dimer may be administered over a long period of time, i.e., months or even years, without causing harmful side effects. The time intervals for prophylactic or therapeutic administration of the drug may typically range from one or more times daily to weekly and monthly dosages and may also comprise even longer intervals, depending on the respective patient and the urgency of treatment as well as on the efficacy of the lysozyme dimer.

Figure 3:
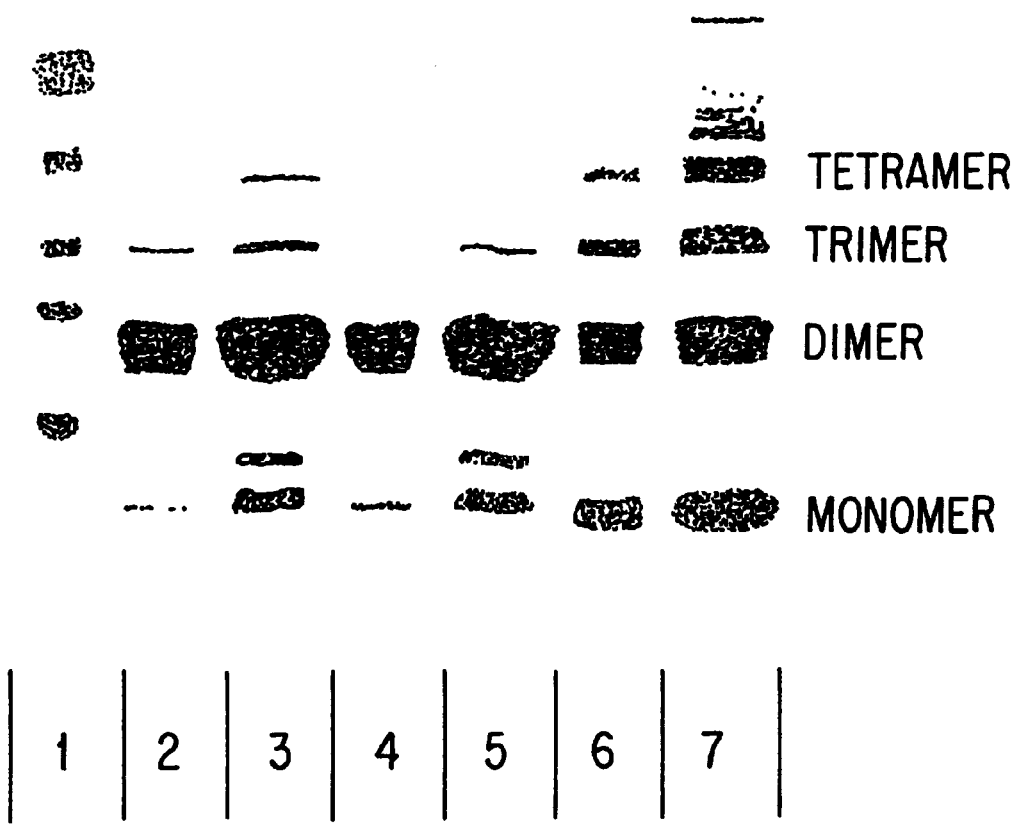
FIG. 3 displays a comparative showing of the purity of lysozyme dimer preparations manufactured according to two different prior art techniques.

As indicated above, the present invention was at least partly made possible through the availability of high grade lysozyme dimer. The striking difference of product quality and, in particular, of the undesired lysozyme monomer share, is demonstrated by FIG. 3:

Lane 1 represents LMW prestained protein standards: Phosphorylase B 142.000 dalton, BSA 97.000, ovalbumin 50.000, carbonic anhydrase 35.100, soybean trypsin inhibitor 29.700, lysozyme 21.900 (Biorad, USA);

lanes 2 and 3 show purified lysozyme dimer LYDIUM KLP®602 (KLP-602 available from Nika Health Products) lot 506449, laboratory control; lane 2 loaded with 6.6 µg and lane 3 with 19.8 µg;

lanes 4 and 5 show another batch of KLP-602, lane 4 loaded with 6.6 µg and lane 5 with 19.8 µg;

lanes 6 and 7 show a lysozyme dimer preparation (KIW-607) manufactured according to Sorrentino et al., Eur. J. Bioch. 124, 183–189 (1982); lane 6 loaded with 6.6 µg and lane 7 with 19.8 µg.

The purified lysozyme dimer preparation KLP-602 contains four times more dimer than the compared product KIW-607, whereas the compared product KIW-607 contains six times more monomer than KLP-602.

In order that the invention described herein may be more fully understood, the following example is set forth. It should be understood that this example is for illustrative purposes only and is not to be construed as limiting this invention in any respect.

EXAMPLE 1:

Lysozyme Dimer (Lydium-KLP) in the Treatment of Cystic Ovarian Disease (COD)

Cystic ovarian disease causes permanent or temporary infertility of cows in many farms. COD occurs with approximately 6 to 50% of the cows in the postcalving period. The etiology of the disease is not yet fully understood even though metabolic disorders and an insufficient immune system have been recognized as major risk factors for the development of COD. Ovarian cysts may cause a stop of menstrual cycles, irregular cycles or even nymphomania. The presence of ovarian cysts is determined by rectal examinations.

Investigations were carried out on 134 cows without signs of cyclicity at least 8 weeks after calving. Among them 69 cows had earlier been treated by other methods, particularly by administration of hormones such as gonadotropin releasing hormone (GnRH), human chorionogonadotropin (HCG), progesterone, and prostaglandine (PGF-2 alfa). The treatment was, however, not always effective.

In the experimental group, Lydium-KLP was administered by intrauterine infusion of 50 ml of a 4% glucose solution comprising 2 mg of lysozyme, either once as a single dose (86 cows) or repeatedly, i.e., with an additional dose on the $14^{th}$ (38 cows) and $28^{th}$ day (10 cows). Every 14 days rectal examination was made. The cows were inseminated in the first estrus after the treatment and 6 weeks later they were examined for pregnancy. The progesterone level was determined by the EIA method in blood samples from 29 cows before and 14 days after the treatment.

RESULTS

The period from calving to the first treatment was 118.4±65.3 days. Rectal examinations made on the $14^{th}$ day after treatment showed total or partial regression of cysts in many animals but also substantially unchanged cysts persisting in some cows. In such cases the Lydium-KLP was infused again. As a result of the first or repeated treatment, 129 cows (96.3%) showed the heat by 21.1±13.6 days. In addition, 60% of the treated cows had estrus before day 21 after the first infusion of Lydium-KLP. Moreover, 102 cows (76.1%) were pregnant by 32.9±20.7 days following the first infusion of Lydium-KLP. The time of the first heat and the percentage of conceived cows as the result of a successful insemination in the first or second heat is illustrated in FIG. 1. The insemination index was 1.46 and 68 cows were pregnant after the first insemination.

Figure 2:
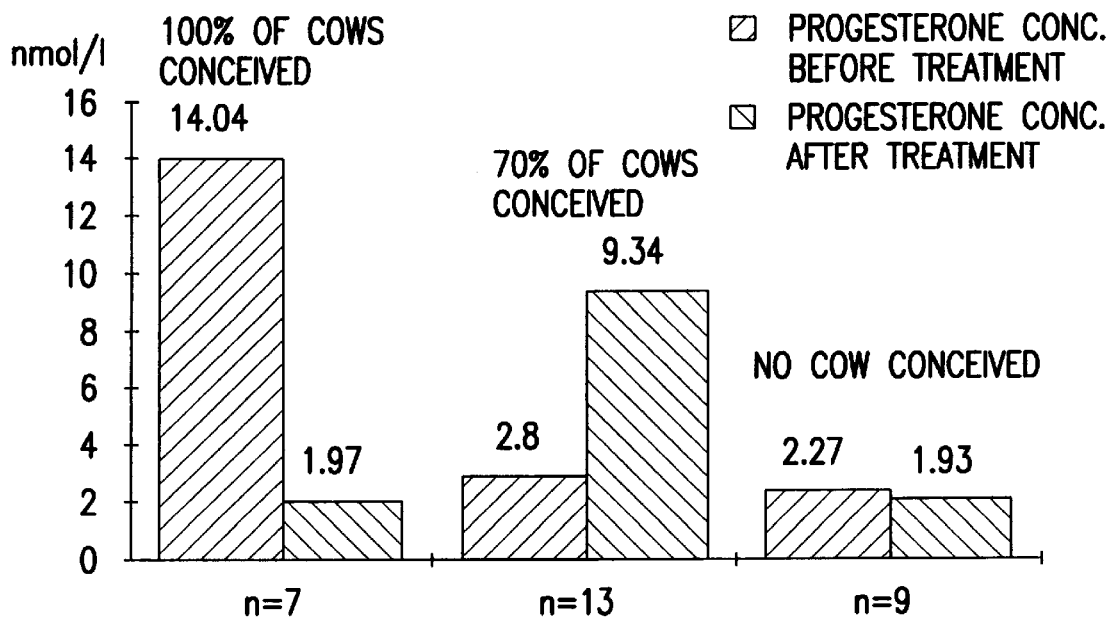
FIG. 2 shows the serum progesterone concentration before and 14 days after intrauterine administration of Lydium-KLP.

The progesterone level before treatment was either low or high (6.7±5.8 nmol/l; see FIG. 2). Surprisingly, after Lydium-KLP intrauterine infusion a modulation of increased or decreased progesterone levels resulting in the re-establishment of physiologically normal values could be observed. FIG. 2 shows the progesterone concentrations before and 14 days after intrauterine infusion of Lydium-KLP and the percentage of conceived cows as the result of an increase or decrease of the progesterone level. Cows with no changes in the progesterone level, however, remained permanently infertile.

This Example shows that Lydium-KLP normalizes metabolic and hormonal ovarian activity in cows and opens new possibilities for an effective prevention or therapy of ovarian cysts in dairy cows.

What is claimed is:

1. A method for prophylactic or therapeutic intervention of ovarian cysts in a cow, comprising administering to a cow in need of such treatment a lysozyme dimer in an amount effective for preventing or treating said ovarian cysts.

2. The method according to claim 1, wherein the method comprises normalization of abnormally high or low progesterone levels.

3. The method according to claim 1, wherein the dimerized lysozyme is administered in the form of an intrauterine infusion.

4. The method according to claim 1, wherein said lysozyme dimer contains about 10% by weight or less of unintended byproducts and is essentially free from a monomeric form of lysozyme.

5. The method according to claim 1, wherein the lysozyme dimer is in a pharmaceutical composition, wherein said pharmaceutical composition is a gel, an ointment or a liquid composition and comprises at least one additive selected from the group consisting of a physiologically acceptable solvent, a carrier, and a suitable preservative.

6. The method according to claim 5, wherein said pharmaceutical composition comprises said lysozyme dimer in an amount of from 0.01 to 10 mg/ml.

7. The method according to claim 6, wherein said pharmaceutical composition comprises said lysozyme dimer in an amount of from 0.01 to 1 mg/ml.

8. The method according to claim 1, wherein said administration comprises multiple doses administered over a period of between 12 hours and three weeks.

9. The method according to claim 1, wherein the effective amount of lysozyme dimer ranges from 1.0 to 100 µg/kg total body weight.

10. A method for treating an abnormally high or low progesterone level in a cow, comprising administering to a cow in need of such treatment a single or repeated dose of lysozyme dimer in an amount effective for normalizing said progesterone level.

11. The method according to claim 10, wherein the effective amount of lysozyme dimer ranges from 1.0 to 100 µg/kg total body weight.

* * * * *